United States Patent [19]

Smith et al.

[11] Patent Number: 5,068,368

[45] Date of Patent: Nov. 26, 1991

[54] STABILIZED LITHIUM ACETYLIDE AND REACTIONS THEREWITH

[75] Inventors: W. Novis Smith; Christopher Louer, both of Philadephia, Pa.

[73] Assignee: Cyprus Foote Mineral Company, Malvern, Pa.

[21] Appl. No.: 521,743

[22] Filed: May 10, 1990

[51] Int. Cl.$^5$ .......................... C07J 7/00; C07J 75/00; C07C 29/143; C07F 1/02

[52] U.S. Cl. ...................... 552/556; 552/592; 552/596; 552/639; 568/874; 568/813; 568/828; 568/838; 568/780; 260/665 R

[58] Field of Search ............... 552/556, 592, 596, 639; 568/874, 813, 828, 838, 780, 874; 260/665 R

[56] References Cited

U.S. PATENT DOCUMENTS

| | | | |
|---|---|---|---|
| 3,065,146 | 11/1962 | Sih et al. | 552/602 |
| 3,166,551 | 1/1965 | Burn et al. | 552/601 |
| 3,506,728 | 4/1970 | Viehe et al. | 568/828 |
| 3,516,991 | 6/1970 | Walker | 552/639 |
| 3,557,220 | 1/1971 | Bach et al. | 568/874 |
| 3,629,298 | 12/1971 | Van Rheenen | 552/534 |
| 4,216,159 | 8/1980 | Hessler et al. | 552/592 |
| 4,320,236 | 3/1982 | Wiederkehr | 568/813 |
| 4,336,054 | 6/1982 | Sjoerdsma | 71/67 |
| 4,526,720 | 7/1985 | Van Rheenen et al. | 552/529 |
| 4,582,644 | 4/1986 | Runge | 552/592 |

OTHER PUBLICATIONS

Feisee and Fieser, Reagents for Organic Sythesis, vol. 1 (J. W. Wiley, N.Y., 1967), pp. 573–575.
Midland, J. Organic Chemistry, 40(15), 1975, pp. 2250 to 2252.
Corbellini et al., Chim & Ind. (Milan), 42, 251–4, 1960, Chemical Abstracts, vol. 54, 1960, Abstract, 19250(f).

*Primary Examiner*—Mukund J. Shah
*Assistant Examiner*—E. C. Ward
*Attorney, Agent, or Firm*—John Lezdey

[57] ABSTRACT

A process for the preparation of ethynyl carbinols of the formula:

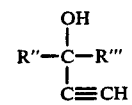

wherein R" is hydrogen, a substituted or unsubstituted aliphatic or aromatic hydrocarbon, R'" is a substituted or unsubstituted aliphatic or aromatic hydrocarbon or R" and R'" together to the carbon atom to which they are joined represent a steroid, which comprises the steps of A. reacting in a solvent system comprising an aromatic hydrocarbon, at least one lithium alkylamide selected from the group consisting of:

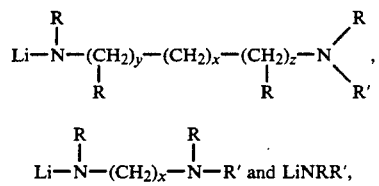

wherein R is a hydrogen or lower alkyl, R' is hydrogen, lower alkyl, a substituted or unsubstituted aliphatic, alicyclic or aromatic hydrocarbon, x is an integer of 2 to 8, y and z are each 0 to 1, with acetylene to form a monolithium acetylide B. reacting in a solvent system comprising an aromatic hydrocarbon, the monolithium acetylene from Part A with a ketone of the formula R"R'"C=O, wherein R" and R'" are as hereinbefore defined, and then C. hydrolysing the reaction product of Part B to form the corresponding ethynyl carbinol compound.

12 Claims, No Drawings

STABILIZED LITHIUM ACETYLIDE AND REACTIONS THEREWITH

FIELD OF THE INVENTION

The present invention relates to the preparation of lithium acetylide from lithium alkylamides and the reaction of lithium acetylide with aldehydes and ketones. More particularly, the invention relates to a process for the preparation of ethynyl carbinols from stable solutions of lithium alkylamides in a single reaction vessel and at higher temperatures.

BACKGROUND OF THE INVENTION

Monolithium acetylide is a valuable reagent for the preparation of ethynyl carbinols and terminal acetylenes. Monolithium acetylide has been used to ethynylate 17-keto steroids unsubstituted in the $C_{16}$ position. However, it was previously necessary to utilize tetrahydrofuran (THF) or other etheral solvents to prepare the reagent. Such solvents cause problems in commercial scale processes.

It is well known to prepare 17-keto, 3-keto or 3, 17-diketo steroids with substituents on the A, B or C rings, see for example U.S. Pat. Nos. 3,166,551; 3,065,146; 3,516,991; 3,629,298 and 4,216,159.

M. M. Midland in J. Org. Chem. 40, 2250 (1975) reported reacting n-butyllithium with acetylene in THF at low temperatures ($< -70°$) and in dilute solutions to produce monolithium acetylide. (See also Fieser and Fieser, Reagents for Organic Synthesis, Vol. 1, Wiley, New York, 1967, p. 573). Midland found that warming or attempting to generate a more concentrated solution resulted in disproportionation to the insoluble dilithium acetylide and acetylene. This disproportionation is an important disadvantage and occurs in the absence of a complexing agent. (See Corbellini et al, Chem. Ind. (Milan) 42, 251 (1960) and Chem. Abstr. 54, 19250 (1960)).

To reduce or prevent the disproportionation, the monolithium acetylide is usually prepared in liquid ammonia, which presumably serves as an appropriate complexing agent. An amine such as ethylenediamine can also be used to stabilize monolithium acetylide. Ethylenediamine so greatly stabilizes monolithium acetylide that monolithium acetylide is sold commercially as a solid ethylenediamine complex. Ethylenediamine, while stabilizing monolithium acetylide to the point that it can be sold commercially, actually reduces the reactivity of the catalyst to the point that it is not useful for many ethynylation procedures.

U.S. Pat. No. 4,005,562 discloses the use of monolithium acetylide to ethynylate 17-keto steroids unsubstituted in the $C_{16}$ position. The monolithium acetylide was prepared by bubbling acetylene into THF held at $-70°$ C. under anhydrous conditions followed by addition of butyllithium. The 17-keto steroid was added to the unstabilized monolithium acetylide, and the mixture stirred for 3 hours at $-70°$ C. to produce the 17α-ethynyl-17β-hydroxy steroid product.

U.S. Pat. No. 4,320,236 discloses the use of a monolithium acetylide-ammonium complex (which is well known to those skilled in the art) to ethynylate ketones at below about $-30°$ C. The examples in U.S. Pat. No. 4,320,236 disclose ethynylation reaction temperatures of $-50°$ to $10°$ C. The unsaturated acyclic ketones ethynylated in U.S. Pat. No. 4,320,236 are very reactive whereas the monolithium acetylide reagent produced by the process of the present invention is reactive with steroidal 17-ketones which are highly substituted sterically hindered ketones such as cyclopentanones, that are ordinarily much less reactive.

U.S. Pat. No. 4,526,720 to Van Rheenen et al discloses a one pot and a two pot process for preparing monolithium acetylide. Each reaction involves contacting an organolithium compound with a solution containing acetylene in the presence of a stabilizing amine. The amine reacts with the organolithium compound to form a lithium complex and/or a corresponding lithium amide which is subsequently reacted with acetylene.

U.S. patent application Ser. No. 374,740, filed June 30, 1989, entitled, "Stable Lithium Amides and Reagent Compositions Thereof" of W. Novis Smith, which is herein incorporated by reference, discloses lithium amide reagent compositions with aromatic solvents which can be used in the process of the present invention.

The use of lithium acetylide in various forms is well known particularly for the formation of ethynyl alcohols from the reaction with ketones and aldehydes. In many of these cases, the lithium acetylide must be formed in solvents such as tetrahydrofuran, which are less desirable to use due to expense, or necessitate the use of extensive refrigeration (liquid ammonia), or require the use of a solid lithium acetylide/ethylene diamine complex or lithium amide. On a commercial scale, it is more desirable and more cost efficient to use liquid reagents or concentrated solutions of reagents which are stable. The use of storable solutions of lithium dialkylamides in aromatic solvents is the focus of this invention.

SUMMARY OF THE INVENTION

The present invention relates to the preparation of lithium acetylide by the use of at least one lithium alkylamide in a solvent comprising an aromatic solvent and the subsequent reaction of aldehydes and/or ketones with the lithium acetylide formed. These aromatic solutions of lithium alkylamides are storable, concentrated and can be shipped without refrigeration. More particularly, the invention relates to a process for reacting ketones and other carboxyl-containing compounds with lithium acetylides in a media comprising aromatic solvents, which acetylides are derived from one or more lithium alkylamides. The reactions can all take place in the same reaction vessel and solvent without the need of any ethers, extra amines or stabilizers other than those formed from the lithium alkylamides. (These solvents may be added in certain special cases). Surprisingly, the reaction to form the carbonyl compounds may be performed at higher temperatures, for example at ambient temperatures, preferably between about $0°$ and $20°$ C.

The reactions involved in the process of the invention are as follows:

-continued

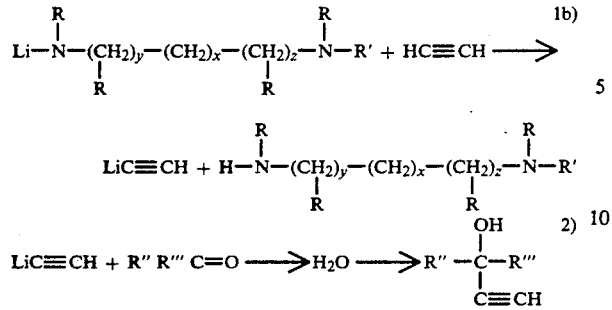

wherein R hydrogen or lower alkyl, and R' can be hydrogen, alkyl or any aliphatic or aromatic hydrocarbon which is substituted or unsubstituted or R and R' together to the nitrogen atom to which they are attached is a 6-8 membered cycloaliphatic group, x is an integer of 2 to 8, x and z are each 0 or 1, and R" and R'" are as hereinafter described. Solvents such as THF, ether, tertiary amines or other hydrocarbons may also be added.

The process of the invention produces a stabilized monolithium acetylide reagent which can be prepared and reacted with aldehydes or ketones at up to 30° C. The amine formed in the reaction stabilizes and solubilizes the formed lithium acetylide. The reagent is sufficiently reactive to react with sterically hindered ketones such as 16α- and 16β-methyl and methylene-17-ketosteroids to produce the desired 16-substituted-17α-ethynyl-17β-hydroxy-steroids in high yields.

Surprisingly, the rate of addition of the aldehyde or ketone into the reaction mixture has little or no effect on the reaction or the amount of final yield.

DETAILED DESCRIPTION OF THE INVENTION

Pursuant to the present invention, at least one lithium alkylamide selected from the group consisting of: Li N R R',

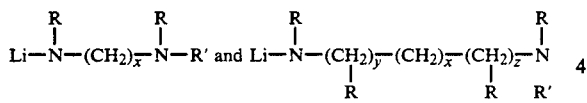

in a solvent comprising an aromatic hydrocarbon is reacted with acetylene gas at a temperature of 30° C. or less in an inert atmosphere to produce stabilized monolithium acetylide. These lithium alkylamides provide an advancement over the prior art since they have better stability, and are soluble in high concentration and do not require the presence of tetrahydrofuran or other ethers.

The monolithium acetylide need not be isolated and the entire reaction mixture can be reacted with an aldehyde or ketone in a similar aromatic solvent to cause ethynylation of the aldehyde or ketone which after hydrolysis forms a compound of the general formula:

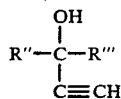

The hydrolysis of the ethynyl compound can be effected in a known manner, e.g., with dilute sulfuric acid, acetic acid, water, ammonium chloride, and the like, to form the ethynyl carbinol.

R" can be hydrogen or lower alkyl ($C_1$-$C_4$), R'" can be hydrogen, alkyl or any aliphatic, alicyclic or aromatic hydrocarbon groups which can be unsubstituted or substituted. Among the preferred groups are alkyl, alkenyl, alkynyl, cycloalkyl, cycloalkenyl, aryl, aryl-lower alkyl, aryl-lower alkenyl, cycloalkyl-lower alkyl and cycloalkenyl-lower alkenyl. In accordance with another embodiment of the invention, the aforementioned aryl, cycloalkyl or cycloalkenyl groups can be unsubstituted or substituted in at least one position with one or more substituents selected from the group consisting of lower alkyl, lower alkoxy, halo, trifluoromethyl, amino, hydroxyl and carboxyl.

The term "aliphatic hydrocarbon" includes open chain aliphatic and cycloaliphatic hydrocarbons as well as hydrocarbons containing both aliphatic and cycloaliphatic moieties. In accordance with a preferred embodiment of the invention, R and R' are an alkyl radical containing 1 to 20 carbon atoms such as methyl, ethyl, isopropyl, n-propyl, octadecyl, 6-methyl-10-ethylhexadecyl, etc. The term alkenyl designates alkenyl groups having at least one olefinic double bond and containing from 2 to 20 carbon atoms such as vinyl, allyl, 5-octenyl, 2,3-dimethyl-4-octenyl, 8-hexadecenyl, 5,6-dimethyl-7-hexadecenyl, 5,6-dimethyl-7-hexadecenyl, etc. The term alkynyl includes alkynyl groups having at least one triple bond and containing from 3 to 20 carbon atoms such as propynyl, 3,7-dimethyl-5-octynyl, 6-heptadecynyl, etc.

Cycloalkyl groups which are designated by R and R' generally contain from 3 to 8 carbon atoms, such as cyclopropyl, cyclohexyl and the like. The cycloalkenyl groups designated by R contain from 3 to 8 carbon atoms, such as cyclopropenyl, cyclohexenyl, etc. The term "aryl" includes aromatic, monocyclic or bicyclic residues which can, if desired, contain a hetero atom in the ring. Among the preferred hetero atoms are sulfur, oxygen and nitrogen. The preferred aromatic residues are phenyl, naphthyl, pyridinyl, and the like.

The term "lower alkyl" includes saturated aliphatic hydrocarbon radicals containing from 1 to 7 carbon atoms such as methyl, ethyl, n-propyl, isopropyl, etc. The term "lower alkenyl" designates lower alkenyl radicals containing from 2 to 7 carbon atoms such as vinyl, allyl, etc. The term "lower alkoxy" includes lower alkoxy radicals containing from 1 to 7 carbon atoms such as methoxy, isopropoxy, ethoxy, etc.

When the aryl, cycloalkyl or cycloalkenyl groups are substituted, they can be preferably substituted in at least one portion, particularly from one to four positions with either lower alkyl or lower alkoxy substituents.

R" can be hydrogen or R" and R'" can be the same as R or R' or R" and R'" together with the carbon atom to which they are joined represents 3- and/or 17-keto steroids such as androstenedione, 16-methylene-17-keto steroids, or the like.

The aromatic solvents which may be used in the present invention include benzene, toluene, ethyl benzene, cumene, xylene diisopropyl benzene, and the like.

The aromatic solvent may be used alone or in admixture with hydrocarbons such as cycloalkanes, more particularly, cyclopentane, cyclohexane, or the like, or aliphatic hydrocarbons such as hexane, heptane, or the like. It is also understood that tetrahydrofuran and other ethers may be added to the solvent, although, this is not preferred.

Advantageously, the reactions can be performed in the same reaction vessel without separation and in the same solvent since it is well known that allowing the monolithium to stand even at −78° C. for 6 hours with an atmosphere of acetylene may lower the yield 10%. In the past, a stabilizing amine was utilized to form a complex with the monolithium acetylide but the additional amine is not necessary in the present invention. Also, the presence of mixed solvents as proposed in the prior art made it difficult to recover the solvent and the product.

Examples of suitable compounds which may be used in the invention to prepare the corresponding ethynyl carbinol include:

| | |
|---|---|
| Cyclopentanone | Acetaldehyde |
| Cyclohexanone | 4-Androstene-3,17-dione |
| Cycloheptanone | 4-Androstene-17-one |
| Acetone | Isophorone |
| 2-Butanone | Mesityl oxide |
| 3-Pentanone | Benzal acetone |
| Fenchone | Dibenzal acetone |
| 2- or 3-Octanone | Acetophenone |
| Diisopropyl ketone | Propiophenone |
| 2-Cyclohexylcyclohexanone | Benzophenone |
| 3-Cyclohexylcyclohexanone | 9-Fluorenone |
| Benzaldehyde | 1-Indanone |
| | Tetralone |

It has been found that lithium acetylide formed from a mixture of the various lithium dialkylamides in a solvent comprising an aromatic hydrocarbon wherein at least 5% of the mixture is a hydrocarbon soluble lithium dialkylamide preferably a diamine derivative, will give higher yields with aldehydes or ketones than when an insoluble lithium dialkyl amide is used.

The following examples are given to illustrate the present invention and are not to be construed as limiting the scope thereof in any manner. All parts and percentages referred to herein are by weight unless otherwise indicated.

EXAMPLE 1

A. Preparation of Lithium Diisobutylamide

Following the process disclosed in application Ser. No. 374,740, 0.22 moles of diisobutyl amine was added to 100 ml of a 2.2M solution of n-butyl lithium in toluene. A clear solution of lithium diisobutylamide was obtained.

In lieu of lithium diisobutylamide there may be substituted or added lithium dimethylaminopropylamide.

B. Preparation of Lithium Acetylide and Reaction with Ketone

The reaction mixture of Part A was placed without isolation under a nitrogen atmosphere at −60° C. and then saturated with acetylene to produce lithium acetylide. The solution was then permitted to warm to 10° C.

C. A solution of 0.18 mole diisopropyl ketone in 50 ml of toluene was added to the reaction mixture of Part B (used lithium dimethylamino propylamide) over a 30 minute period at 10° C. While stirring, the solution was warmed to room temperature. The reaction product was then hydrolyzed by treatment with 50 ml of water. Then anhydrous sodium sulfate was added.

Gas chromatographic analysis showed a yield of 83% diisopropylethynyl carbinol.

EXAMPLE 2

The procedure of Example 1 was followed except that in Part C the ketone was added to the lithium acetylide (from lithium dimethylamine propylamide) solution of Part B over a period of 3 minutes. After hydrolysis, diisopropylethynyl carbinol was obtained at a yield of 77%.

EXAMPLE 3

Preparation of Lithium Alkyl Amides, Formation of the Lithium Acetylide and Subsequent Reaction with a Ketone (Standard)

A. 20.4 g (0.2 moles) of dimethylaminopropyl amine (DMAPA) were added to 100 ml (0.2 mole) of a 2.0M toluene solution of n-butyllithium under nitrogen with stirring. The solution was cooled to −30° C. and acetylene gas was passed into the solution until it was saturated. (The acetylene was passed initially over alumina to remove acetone.)

B. The acetylene atmosphere was maintained while 17.1 g (0.15 moles) of diisopropyl ketone dissolved in 50 ml toluene were added at −30° C. over a one hour period. When the addition was completed, the solution was permitted to warm up over 30 minutes and then 20 ml of water were added. About 10–15 g of anhydrous sodium sulfate was added and the saturated salt layer allowed to settle. To this hydrocarbon solution was then added 10.0 g 1-octanol and a sample of the solution injected into a gas chromatograph. The ratio of the peaks for product and the 1-octanol standard was corrected for response difference (1.1 times the 1-octanol peak). The yield of the ethynyl alcohol was 93%.

EXAMPLE 4

Simultaneous Addition of Lithium Acetylide/Amide and Ketone

A solution of lithium acetylide/dimethylaminopropyl amine (DMAPA) was prepared by the addition of acetylene gas to a 2.0 molar solution of lithium dimethylaminopropyl amide at room temperature until it was saturated. 100 ml (0.20 moles) of this clear solution was added to a stirred flask under a nitrogen/acetylene atmosphere over a one hour period at the same rate that 17.1 g (0.15) of diisopropyl ketone in 100 ml toluene were added to the same flask. The flask had 50 ml toluene in it initially before the reaction was started. The reaction flask was maintained at 10° C. The reaction mixture was stirred for 30 minutes after the addition was finished and 20 ml water added while stirring. Then 10–15 g anhydrous sodium sulfate and 10.0 g 1-octanol were added. The yield was found to be 98% by gas chromatography.

EXAMPLE 5

Following the procedure of Example 3, a series of experiments were performed with compounds containing a keto group to obtain the corresponding ethynyl carbinol. The results are summarized in Table 1.

TABLE 1

Reaction of Acetylenes and Soluble Lithium Alkylamides in Toluene with Ketones

| Lithium Alkylamide | Ketone | Temp. °C. | % Yield |
|---|---|---|---|
| A. dimethylaminopropyl amine (DMAPA) | diisopropyl ketone | −30 | 93 |
| B. dimethylaminopropyl | diisopropyl | −30 | 93[1] |

TABLE 1-continued

Reaction of Acetylenes and Soluble Lithium Alkylamides in Toluene with Ketones

| | Lithium Alkylamide | Ketone | Temp. °C. | % Yield |
|---|---|---|---|---|
| | amine (DMAPA) | ketone | | |
| C. | dimethylaminopropyl amine (DMAPA) | diisopropyl ketone | −30 | 82[2] |
| D. | dimethylaminopropyl amine (DMAPA) | diisopropyl ketone | 35 | 52 |
| E. | dimethylaminopropyl amine (DMAPA) | diisopropyl ketone | 10 | 83[3] |
| F. | dimethylaminopropyl amine (DMAPA) | diisopropyl ketone | 10 | 77[3] |
| G. | dimethylaminopropyl amine (DMAPA) | fenchone | 10 | 62 |
| H. | dimethylaminopropyl amine (DMAPA) | acetophenone | −30 | 73 |
| I. | dimethylaminopropyl amine (DMAPA) | cyclo-hexanone | 20 | 57 |
| J. | dimethylaminopropyl amine (DMAPA) | cyclo-hexanone | 20 | 59 |
| K. | N,N,N'-trimethyl ethylene diamine | diisopropyl ketone | −30 | 84 |
| L. | N,N,N'-trimethylpropylene diamine | diisopropyl ketone | −30 | 87 |
| M. | diisopropyl amine | diisopropyl ketone | −30 | <5 |
| N. | 80% diisopropyl amine 20% DMAPA | diisopropyl ketone | 20 | 50 |
| O. | diisobutyl amine | diisopropyl ketone | −30 | 49[4] |

[1] 100% Excess Ketone
[2] Inverse Addition
[3] 3 min. Ketone Addition - Lithium acetylide/amide solution was premixed and stored for two weeks before reacting with ketone
[4] 20 ml THF added

EXAMPLE 6

Following the procedure of Example 4, a series of experiments were preformed with compounds containing a keto group to obtain the corresponding ethynylcarbinol. The results are summarized in Table 1.

TABLE 2

| Sample | Ketone | Temp. °C. | % Yield |
|---|---|---|---|
| A. DMAPA | diisopropyl ketone | 10 | 98 |
| B. DMAPA | diisopropyl ketone | 10 | 93 |
| C. DMAPA | fenchone | 10 | 68 |
| D. DMAPA | progesterone | 10 | 85 (isolation) |

EXAMPLE 7

Reaction of Lithium Acetylide with Bromooctane

A solution of lithium acetylide/DMAPA was prepared by the addition of acetylene gas to a 100 ml of a 2.0 molar solution of lithium DMAPA in toluene until saturated at room temperature. 0.18 moles of n-bromooctane was added and the solution stirred for 24 hours at room temperature and then hydrolyzed. The yield of 1-decyne was 75% with approximately 20% unreacted starting material.

I claim:

1. In a process for the preparation of ethynyl carbinols of the formula:

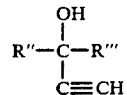

wherein R" is hydrogen or lower alkyl, R'" is hydrogen, alkyl, a substituted or unsubstituted aliphatic, alicyclic or monocyclic or bicyclic aromatic hydrocarbon or R" and R'" together to the carbon atom to which they are joined represent a steroid, which comprises the steps of A. reacting in a solvent system at least one lithium alkylamide selected from the group consisting of:

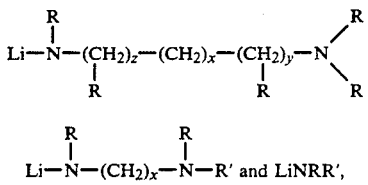

wherein R is a hydrogen or lower alkyl, R' is hydrogen, lower alkyl, a substituted or unsubstituted aliphatic, alicyclic or monocyclic or bicyclic aromatic hydrocarbon, x is an integer of 2 to 8, y and z are each 0 to 1, with acetylene to form a monolithium acetylide B. reacting in a solvent system the monolithium acetylene from Part A with a ketone of the formula R"R'" C=O, wherein R" and R'" are as hereinbefore defined, and then C. hydrolysing the reaction product of Part B to form the corresponding ethynyl carbinol compound, the improvement comprising the solvent system in Parts B comprises a moncyclic aromatic solvent in an amount sufficient to solubilize said lithium alkylamide and to effect a stable solution.

2. The process of claim 1 wherein the reactions are performed in a single reaction vessel without separation.

3. The process of claim 1 wherein the aromatic solvent is selected from the group consisting of benzene, toluene, xylene, ethyl benzene and isopropyl benzene.

4. The process of claim 1 wherein said lithium amide is lithium dialkylaminoalkylene amide.

5. The process of claim 1 wherein the lithium alkylamide is selected from the group consisting of lithium diisobutylamide and lithium diisopropylamide.

6. The process of claim 1 wherein the reaction of Part B is performed up to ambient temperature.

7. The process of claim 5 wherein the reaction temperature is between about 0° and 20° C.

8. The process of claim 1 wherein R" and R'" together with the carbon atom to which they are attached represent a steroid.

9. The process of claim 7 wherein said steroid is a 17-keto steroid.

10. The process of claim 7 wherein said steroid is a 16-methylene-17-keto steroid.

11. The process of claim 1 wherein the reaction of Part B and Part C as simultaneous.

12. In a process for the preparation of a stabilized monolithium acetylene comprising the step of reacting in a solvent system least one lithium alkylamide selected from the group consisting of:

LiNRR',

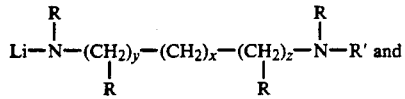

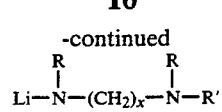

wherein R is hydrogen or lower alkyl, R' is hydrogen, lower alkyl, a substituted or unsubstituted aliphatic, alicyclic or monocyclic or bicyclic aromatic hydrocarbon, x is an integer of 2 to 8, y and z are each 0 to 1, with acetylene the improvement in that said solvent system essentially consists of a monocyclic aromatic solvent in an amount sufficient to solubilize said lithium alkylamide and to effect a stable solution.

* * * * *